(12) United States Patent
Yang et al.

(10) Patent No.: US 12,303,616 B2
(45) Date of Patent: May 20, 2025

(54) ANTI-THROMBOTIC AND ENDOTHELIALIZATION-ENHANCED BIOPROSTHETIC VALVE MATERIAL AND PREPARATION METHOD THEREOF

(71) Applicant: Sichuan University, Chengdu (CN)

(72) Inventors: Li Yang, Chengdu (CN); Yunbing Wang, Chengdu (CN); Rifang Luo, Chengdu (CN); Xingdong Zhang, Chengdu (CN)

(73) Assignee: Sichuan University, Chengdu (CN)

( * ) Notice: Subject to any disclaimer, the term of this patent is extended or adjusted under 35 U.S.C. 154(b) by 475 days.

(21) Appl. No.: 17/235,952

(22) Filed: Apr. 21, 2021

(65) Prior Publication Data

US 2021/0322641 A1    Oct. 21, 2021

(30) Foreign Application Priority Data

Apr. 21, 2020    (CN) .......................... 202010317451.3

(51) Int. Cl.
    *A61L 27/36*    (2006.01)
    *A61L 27/24*    (2006.01)

(52) U.S. Cl.
    CPC .......... *A61L 27/3687* (2013.01); *A61L 27/24* (2013.01); *A61L 27/3625* (2013.01);
(Continued)

(58) Field of Classification Search
    CPC .. A61L 27/3687; A61L 27/24; A61L 27/3625; A61L 2300/802; A61L 2430/20; A61L 2430/40
(Continued)

(56) References Cited

U.S. PATENT DOCUMENTS

| | | | | | |
|---|---|---|---|---|---|
| 5,306,500 | A | * | 4/1994 | Rhee ..................... | C08H 1/06 424/487 |
| 6,166,184 | A | * | 12/2000 | Hendriks ............ | A61L 27/3687 8/94.11 |
| 2008/0020012 | A1 | * | 1/2008 | Ju ......................... | A61L 27/24 600/365 |

FOREIGN PATENT DOCUMENTS

| | | | |
|---|---|---|---|
| CN | 103122027 B | * | 5/2014 |
| CN | 103030831 B | * | 6/2014 |

OTHER PUBLICATIONS

Attia et al., Surgical pericardial heart valves: 50 Years of evolution, International Journal of Surgery, vol. 94 (2021), pp. 1-9.*

(Continued)

*Primary Examiner* — Jennifer M. H. Tichy
(74) *Attorney, Agent, or Firm* — Bayramoglu Law Offices LLC

(57) ABSTRACT

An anti-thrombotic and endothelialization-enhanced bioprosthetic valve material and preparation thereof are provided. The preparation method includes the following steps: immersing a glutaraldehyde cross-linked bioprosthetic valve material in functional reagent solution for 1-24 h, adjusting pH value of the solution to 3-8, removing it from solution and cleaning with deionized water. The new valve material of the present invention can effectively reduce the toxicity and side effects of the existing glutaraldehyde cross-linked bioprosthetic valve material and effectively reduce thrombosis, along with enhanced endothelialization. The material prepared can be used for pulmonary valve, aortic valve, mitral valve, tricuspid valve, venous valve and other cardiovascular implantable medical devices.

6 Claims, 2 Drawing Sheets
Specification includes a Sequence Listing.

(52) U.S. Cl.
CPC ..... *A61L 2300/802* (2013.01); *A61L 2430/20* (2013.01); *A61L 2430/40* (2013.01)

(58) Field of Classification Search
USPC ........................................................ 424/569
See application file for complete search history.

(56) References Cited

OTHER PUBLICATIONS

Flameng et al., A randomized assessment of an advanced tissue preservation technology in the juvenile sheep model, J Thorac Cardiovasc Surg., Jan. 2015;149(1):340-5.*
Naimark et al., Correlation of structure and viscoelastic properties in the pericardia of four mammalian species, American Journal of Physiology, Oct. 1992; 263(4 Pt 2):H1095-106.*

* cited by examiner

ANTI-THROMBOTIC AND ENDOTHELIALIZATION-ENHANCED BIOPROSTHETIC VALVE MATERIAL AND PREPARATION METHOD THEREOF

CROSS REFERENCE TO THE RELATED APPLICATIONS

This application is based upon and claims priority to Chinese Patent Application No. 202010317451.3, filed on Apr. 21, 2020, the entire contents of which are incorporated herein by reference.

TECHNICAL FIELD

The present invention belongs to the technical field of biomedical materials for cardiovascular implantable devices, and in particular to bioprosthetic valve material with enhanced endothelialization and anti-thrombotic properties and a preparation method thereof.

BACKGROUND

Valvular heart disease is a common disease symbolized by valvular degeneration, which is characterized by narrowing of blood access or valvular insufficiency. Treatment of valvular heart disease includes open-chest heart valve replacement and percutaneous heart valve replacement (PHVR). Many patients cannot accept open-chest surgery due to its shortcomings of large trauma, high risk, slow recovery, and needing for extracorporeal circulation support. PHVR has become the preferred course of future valve surgery because of its reduced trauma and low risk.

Bioprosthetic heart valve is a biomedical material used to replace the human diseased heart valve. It is generally prepared by a process of cross-linking porcine pericardium, bovine pericardium or the like using glutaraldehyde. The process has the advantages of simple operation, low cost and high degree of collagen cross-linking, thus becoming the preferred choice for chemical cross-linking of bioprosthetic heart valves. However, a bioprosthetic heart valve obtained by cross-linking using glutaraldehyde generally has an effective service life of about 10-15 years, because aldehyde groups residual on the valve leaflets cause certain toxicity and calcification problems. Additionally, when the valve material is used for pulmonary valve and venous valve, blood coagulation easily occurs due to the slow blood flow, which is not conducive to its long-term safe use.

SUMMARY

In view of the above problems existing in the prior art, the present invention provides an anti-thrombotic and endothelium-enhanced bioprosthetic valve material and a preparation method thereof, which can effectively reduce the toxicity and side effects of existing glutaraldehyde cross-linked bioprosthetic valve material and effectively reduce the problem of blood coagulation.

In order to achieve the above objective, the technical solution adopted by the present invention to solve the technical problem is as follows.

A preparation method of an anti-thrombotic and endothelium-enhanced bioprosthetic valve material, including the following steps:

immersing a glutaraldehyde cross-linked bioprosthetic valve material in a recombinant human type III collagen solution for 1-24 h, taking out and cleaning with deionized water.

Further, the bioprosthetic valve material is an aortic valve, a pulmonary valve, a venous valve, a tricuspid valve, a mitral valve or an artificial myocardial patch.

Further, the glutaraldehyde cross-linked bioprosthetic valve material is prepared by immersing an animal-derived pericardial biomaterial in an aqueous solution or phosphate buffer saline (PBS) with a volume concentration of 0.1-10% glutaraldehyde (referred to as glutaraldehyde solution) for 4-38 h; preferably, the volume concentration of the glutaraldehyde solution is 0.6% and a soaking time is 24 h.

Further, the animal-derived pericardial biomaterial is a bovine pericardium, a porcine pericardium or a sheep pericardium.

Further, a concentration of the recombinant human type III collagen solution is 1-30 mg/mL, preferably 30 mg/mL, and a soaking time in the recombinant human type III collagen solution is 24 h.

Further, a primary structure of the recombinant human type III collagen is O-free (hydroxyproline), has cellular adhesion properties, and is preferably a collagen tripeptide fragment (GER) containing cellular adhesion functions, but does not contain collagen-mimetic peptides as shown in SEQ ID NO: 2 that specifically bind to α2β1 integrin on a platelet surface.

Further, a core sequence of an amino acid sequence of the recombinant human type III collagen is the polypeptide as shown in SEQ ID NO: 1. The core sequence may be modified, and the sites and groups wherein the modification is performed include, but are not limited to, a mercapto terminal (—SH), a terminal double bond and methacrylate.

Further, the preparation method also includes immersing the deionized water-cleaned material in a reducing agent solution for 0.1-24 h, then removing it from the solution and cleaning with deionized water.

Further, a concentration of the reducing agent solution is 20-100 mg/mL, preferably 50 mmol/L, and a preferred soaking time is 24 h.

Further, the reducing agent is sodium borohydride, potassium borohydride or sodium cyanoborohydride.

The anti-thrombotic and endothelium-enhanced bioprosthetic valve material and the preparation method thereof of the present invention have the following advantages.

In the present invention, the glutaraldehyde cross-linked bioprosthetic valve material is modified by recombinant human type III collagen, in which the recombinant human type III collagen is attached to the glutaraldehyde cross-linked biomaterial through carbon-nitrogen double bond and single bond by the reaction of amino groups in the recombinant human type III collagen and residual aldehyde groups in the glutaraldehyde cross-linked biomaterial. Through the modification of residual aldehyde groups, the toxicity and calcification of biomaterials related to aldehyde groups can be reduced. Additionally, since the recombinant human type III collagen has the identical structure as that in the human body, which has the characteristics of low immunogenicity, the modification method using recombinant human collagen will improve the biocompatibility of animal-derived biological heart valves.

The recombinant human type III collagen in the present invention is a collagen functional area obtained by screening and biosynthesis, which has the same structure as human type III collagen, has no significant cytotoxicity and has low immune rejection in the human body. It has carboxyl, amino, guanidine and other functional groups, its structure has concentrated positive and negative charges, thereby having high water solubility and cell adhesion activity. Different from traditional collagen, the present invention develops the recombinant human type III collagen with anticoagulant properties, which have high affinity for endothelial cells, and its sequence design avoids the new collagen structure from platelet binding site. It is a customized collagen material that can be used for the modification of cardiovascular materials, and its significance is reflected in that the recombinant human type III collagen not only has extremely low immune rejection, but also has remarkable anticoagulant property. The traditional collagen is a mixture of various types of collagen, and it is difficult to remove the O-containing residues in the structure, resulting in the coagulation of DNA fragments in platelets and thus making it difficult for complete removal of animal amino acid groups in immune response. The primary structure of the recombinant human type III collagen designed by the present invention does not contain O, and the above problem does not occur.

The recombinant human type III collagen designed in the present invention has significant anticoagulant effect, and compared with animal-derived collagen, it can not only reduce the immunogenicity of animal-derived tissue, but also enhance the cell adhesion and anticoagulation, which is conducive to the surface endothelialization of cardiovascular implant devices.

The recombinant human type III collagen in the present invention is introduced into valve materials by covalent binding, thus its stability is well maintained. Through the post-treatment of reducing agent, that is, the reducing agent reacts with carbon-nitrogen double bonds in the recombinant human collagen-modified biomaterial and unreacted aldehyde groups in the modification process to reduce it to a more stable single bond, so as to further improve the bonding stability between the recombinant human collagen and biomaterial, which is beneficial to maintain the long-term effect of collagen.

DETAILED DESCRIPTION OF THE EMBODIMENTS

Example 1

Figure 1A:
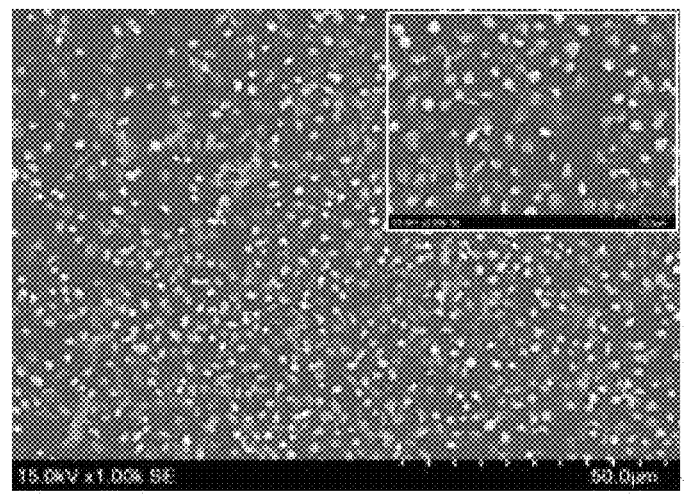
FIG. 1A is a scanning electron microscope (SEM) image showing a platelet adhesion experiment of animal-derived collagen.

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 0.6% for 24 h, to obtain a glutaraldehyde cross-linked animal-derived pericardial biomaterial.
(2) The glutaraldehyde cross-linked animal-derived pericardial biomaterial is cleaned and soaked in a 30 mg/mL recombinant human type III collagen solution for 24 h, then removed from the solution and cleaned with distilled water, where, the amino acid sequence of the recombinant human type III collagen is the polypeptide as shown in SEQ ID NO: 1.

Example 2

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 0.6% for 12 h, to obtain a glutaraldehyde cross-linked animal-derived pericardial biomaterial.
(2) The glutaraldehyde cross-linked animal-derived pericardial biomaterial is cleaned and soaked in a 15 mg/mL recombinant human type III collagen solution for 24 h, then removed from the solution and cleaned with distilled water, where, the amino acid sequence of the recombinant human type III collagen is the polypeptide as shown in SEQ ID NO: 1.

Example 3

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 0.6% for 12 h, to obtain a glutaraldehyde cross-linked animal-derived pericardial biomaterial.
(2) The glutaraldehyde cross-linked animal-derived pericardial biomaterial is cleaned and soaked in a 30 mg/mL recombinant human type III collagen solution for 1 h, then removed from the solution and cleaned with distilled water, where, the amino acid sequence of the recombinant human type III collagen is the polypeptide as shown in SEQ ID NO: 1.
(3) The material obtained in step (2) is soaked in a 50 mmol/L sodium cyanoborohydride ($NaCNBH_3$)-containing PBS for 12 h, and cleaned with distilled water.

Example 4

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 0.6% for 24 h, to obtain a glutaraldehyde cross-linked animal-derived pericardial biomaterial.
(2) The glutaraldehyde cross-linked animal-derived pericardial biomaterial is cleaned and soaked in a 1 mg/mL recombinant human type III collagen solution for 24 h, then removed from the solution and cleaned with distilled water, where, the amino acid sequence of the recombinant human type III collagen is the polypeptide as shown in SEQ ID NO: 1.
(3) The material obtained in step (2) is soaked in a 50 mmol/L sodium borohydride ($NaBH_4$)-containing PBS for 24 h, and cleaned with distilled water.

Example 5

A preparation method of an anti-thrombotic and endothelium-enhanced bioprosthetic valve material includes the following steps.

(1) Fresh porcine pericardium is collected and cleaned, and then soaked in a glutaraldehyde aqueous solution with a volume concentration of 0.6% for 24 h, to obtain a glutaraldehyde cross-linked animal-derived pericardial biomaterial.
(2) The glutaraldehyde cross-linked animal-derived pericardial biomaterial is cleaned and soaked in a 5 mg/mL recombinant human type III collagen solution for 5 h, then removed from the solution and cleaned with distilled water, where, the amino acid sequence of the recombinant human type III collagen is the polypeptide as shown in SEQ ID NO: 1.
(3) The material obtained in step (2) is soaked in a 100 mmol/L potassium borohydride ($KBH_4$)-containing PBS for 1 h, and cleaned with distilled water.

Example 6

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 2% for 12 h, to obtain a glutaraldehyde cross-linked animal-derived pericardial biomaterial.
(2) The glutaraldehyde cross-linked animal-derived pericardial biomaterial is cleaned and soaked in a 2 mg/mL recombinant human type III collagen solution for 12 h, then removed from the solution and cleaned with distilled water, where, the amino acid sequence of the recombinant human type III collagen is the polypeptide as shown in SEQ ID NO: 1.
(3) The material obtained in step (2) is soaked in a 20 mmol/L $NaCNBH_3$-containing PBS for 5 h, and cleaned with distilled water.

Example 7

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 2% for 12 h, to obtain a glutaraldehyde cross-linked animal-derived pericardial biomaterial.
(2) The glutaraldehyde cross-linked animal-derived pericardial biomaterial is cleaned and soaked in a 10 mg/mL recombinant human type III collagen solution for 5 h, then removed from the solution and cleaned with distilled water, where, the amino acid sequence of the recombinant human type III collagen is the polypeptide as shown in SEQ ID NO: 1.
(3) The material obtained in step (2) is soaked in a 50 mmol/L $KBH_4$-containing PBS for 1 h, and cleaned with distilled water.

Example 8

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 0.5% for 24 h, to obtain a glutaraldehyde cross-linked animal-derived pericardial biomaterial.
(2) The glutaraldehyde cross-linked animal-derived pericardial biomaterial is cleaned and soaked in a 20 mg/mL recombinant human type III collagen solution for 10 h, then removed from the solution and cleaned with distilled water, where, the amino acid sequence of the recombinant human type III collagen is the polypeptide as shown in SEQ ID NO: 1.
(3) The material obtained in step (2) is soaked in a 20 mmol/L $KBH_4$-containing PBS for 24 h, and cleaned with distilled water.

Example 9

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 1% for 24 h, to obtain a glutaraldehyde cross-linked animal-derived pericardial biomaterial.
(2) The glutaraldehyde cross-linked animal-derived pericardial biomaterial is cleaned and soaked in a 25 mg/mL recombinant human type III collagen solution for 15 h, then taken out and cleaned with distilled water, where, the amino acid sequence of the recombinant human type III collagen is the polypeptide as shown in SEQ ID NO: 1.
(3) The material obtained in step (2) is soaked in a 60 mmol/L $NaBH_4$-containing PBS for 12 h, and cleaned with distilled water.

Example 10

A preparation method of an anti-thrombotic and endothelium-enhanced bioprosthetic valve material includes the following steps.
(1) Fresh porcine pericardium is collected and cleaned, and then soaked in a glutaraldehyde aqueous solution with a volume concentration of 2% for 24 h, to obtain a glutaraldehyde cross-linked animal-derived pericardial biomaterial.
(2) The glutaraldehyde cross-linked animal-derived pericardial biomaterial is cleaned and soaked in a 10 mg/mL recombinant human type III collagen solution for 24 h, then removed from the solution and cleaned with distilled water, where, the amino acid sequence of the recombinant human type III collagen is the polypeptide as shown in SEQ ID NO: 1.
(3) The material obtained in step (2) is soaked in a 80 mmol/L $NaBH_4$-containing PBS for 16 h, and cleaned with distilled water.

COMPARATIVE EXAMPLE

Preparation of a glutaraldehyde cross-linked bioprosthetic valve: fresh porcine pericardium is collected and cleaned, soaked in a glutaraldehyde aqueous solution with a volume concentration of 0.6% for 24 h, then removed from the solution and cleaned with distilled water.

Experimental Example: Platelet Adhesion Experiment

The material prepared in example 1 is cut into an appropriate size and incubated with platelet-rich plasma for 1 h.

Figure 1B:
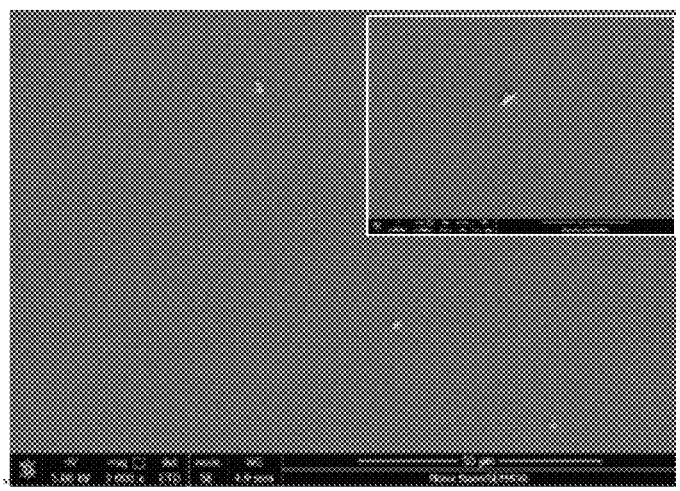
FIG. 1B is a SEM image showing a platelet adhesion experiment of recombinant human type III collagen and animal-derived collagen.

The adhesion of platelets on the material is observed by scanning electron microscope. By scanning electron microscope observation, the SEM image of the platelet adhesion experiment on animal-derived collagen shows that there is a lot of platelet adhesion (FIG. 1A), while the SEM image of the platelet adhesion experiment on recombinant human collagen shows that there is almost no platelet adhesion (FIG. 1B). In FIGS. 1A-1B, the small image in the upper right corner of each image is an enlarged view showing a part of the each image.

Figure 2A:
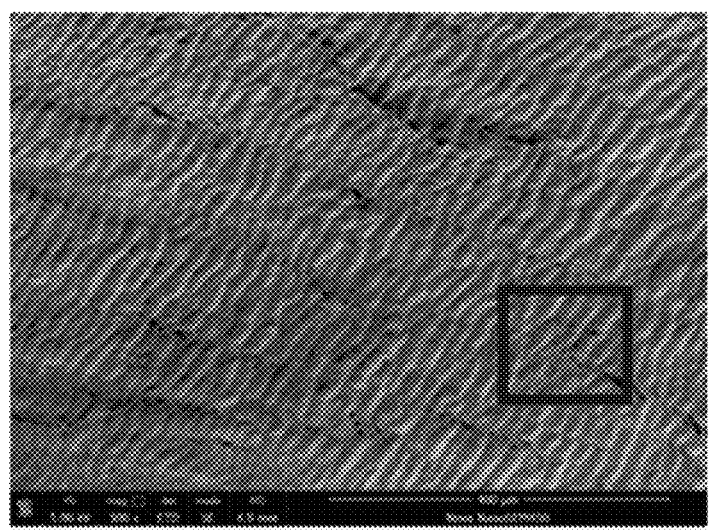
FIG. 2A is a SEM image showing a platelet adhesion experiment of a control group of a glutaraldehyde cross-linked bioprosthetic valve.
Figure 2B:
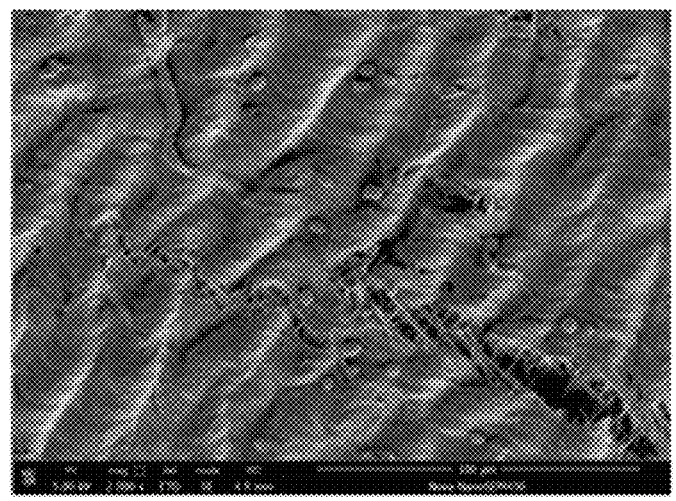
FIG. 2B is an enlarged image of FIG. 2A.
Figure 3A:
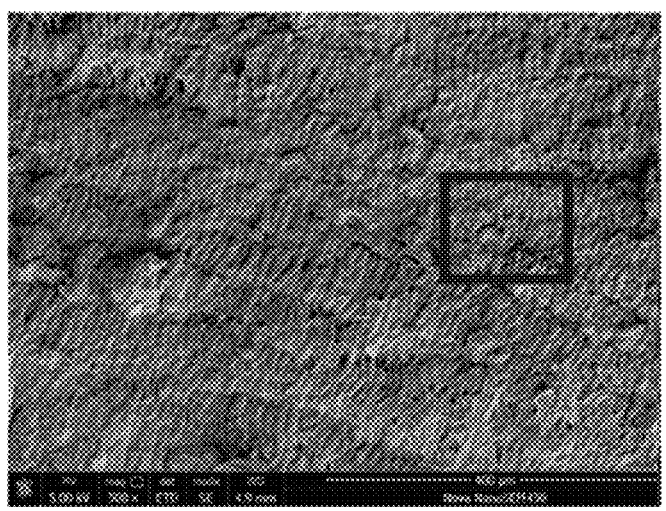
FIG. 3A is a SEM image showing a platelet adhesion experiment of the experimental group in example 1.
Figure 3B:
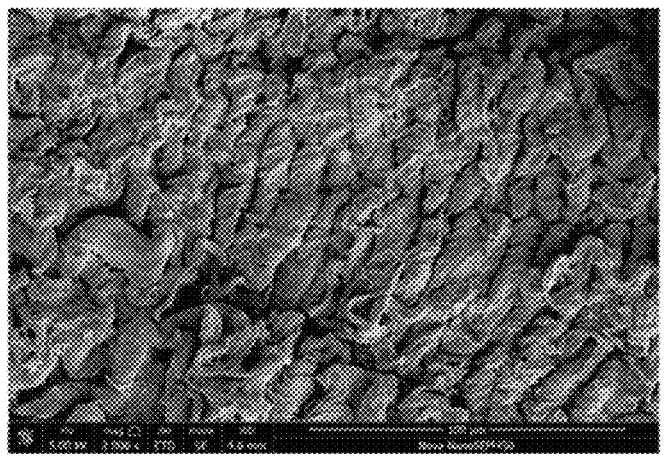
FIG. 3B is an enlarged image of FIG. 3A.

Compared with the control group treated with 0.6% glutaraldehyde (FIGS. 2A-2B), the number of platelets adhered on the surface of the recombinant human collagen-modified bioprosthetic valve (FIGS. 3A-3B) is significantly reduced, indicating that the recombinant human collagen-modified bioprosthetic valve has better anticoagulant performance than the bioprosthetic valve treated with glutaraldehyde alone, which can potentially solve coagulation-related problems such as short service life of bioprosthetic valves due to blood coagulation.

What is claimed is:

1. A preparation method of an anti-thrombotic and surface endothelialization bioprosthetic valve material, comprising the following steps:
   immersing a glutaraldehyde cross-linked bioprosthetic valve material in a 30 mg/mL recombinant human type III collagen solution for 1-24 hours to obtain a first soaked material, taking the first soaked material out of the solution and cleaning the first soaked material with deionized water to obtain a deionized water-cleaned material, wherein the recombinant human type III collagen in the recombinant human type III collagen solution is hydroxyproline-free and does not comprise collagen-mimetic peptides as shown in SEQ ID NO: 2, wherein the glutaraldehyde cross-linked bioprosthetic valve material is prepared by immersing an animal-derived pericardial biomaterial in an aqueous solution or phosphate buffer saline (PBS) with a volume concentration of 0.1-10% glutaraldehyde for 4-38 hours, and
   wherein the animal-derived pericardial biomaterial consists of sheep pericardium.

2. The preparation method of the anti-thrombotic and surface endothelialization bioprosthetic valve material according to claim 1, wherein the recombinant human type III collagen in the recombinant human type III collagen solution has cellular adhesion properties.

3. The preparation method of the anti-thrombotic and surface endothelialization bioprosthetic valve material according to claim 1, wherein the amino acid sequence of the recombinant human type III collagen comprises the polypeptide as shown in SEQ ID NO: 1.

4. The preparation method of the anti-thrombotic and surface endothelialization bioprosthetic valve material according to claim 1, further comprising immersing the deionized water-cleaned material in a reducing agent solution for 0.1-24 hours to obtain a second soaked material, then taking the second soaked material out of the solution and cleaning the second soaked material with deionized water.

5. The preparation method of the anti-thrombotic and surface endothelialization bioprosthetic valve material according to claim 4, wherein a reducing agent in the reducing agent solution is sodium borohydride, potassium borohydride or sodium cyanoborohydride.

6. The preparation method of the anti-thrombotic and surface endothelialization bioprosthetic valve material according to claim 1, wherein the recombinant human type III collagen in the recombinant human type III collagen solution is modified to include one or more of the following: a mercapto terminal (—SH), a terminal double bond and/or methacrylate.

\* \* \* \* \*

```
                     SEQUENCE LISTING

<160> NUMBER OF SEQ ID NOS: 2

<210> SEQ ID NO 1
<211> LENGTH: 30
<212> TYPE: PRT
<213> ORGANISM: Artificial Sequence
<220> FEATURE:
<223> OTHER INFORMATION: The sequence is synthesized.

<400> SEQUENCE: 1

Gly Glu Arg Gly Ala Pro Gly Phe Arg Gly Pro Ala Gly Pro Asn Gly
1               5                   10                  15

Ile Pro Gly Glu Lys Gly Pro Ala Gly Glu Arg Gly Ala Pro
            20                  25                  30

<210> SEQ ID NO 2
<211> LENGTH: 6
<212> TYPE: PRT
<213> ORGANISM: Artificial Sequence
<220> FEATURE:
<223> OTHER INFORMATION: The sequence is synthesized.
<220> FEATURE:
<221> NAME/KEY: MISC_FEATURE
<222> LOCATION: (1)..(6)
<223> OTHER INFORMATION: Xaa = hydroxyproline

<400> SEQUENCE: 2

Gly Phe Xaa Gly Glu Arg
1               5
```